(12) United States Patent
Erb et al.

(10) Patent No.: US 8,586,352 B2
(45) Date of Patent: Nov. 19, 2013

(54) REACTOR SYSTEM AND METHOD FOR PROCESSING A PROCESS FLUID

(75) Inventors: Gary Erb, Crystal Lake, IL (US); David Ross Peterson, Dixon, IL (US); David Penny, Crystal Lake, IL (US)

(73) Assignee: Community Synergies, LLC, Crystal Lake, IL (US)

( * ) Notice: Subject to any disclaimer, the term of this patent is extended or adjusted under 35 U.S.C. 154(b) by 931 days.

(21) Appl. No.: 12/716,799

(22) Filed: Mar. 3, 2010

(65) Prior Publication Data

US 2010/0267125 A1    Oct. 21, 2010

Related U.S. Application Data

(63) Continuation-in-part of application No. 12/189,468, filed on Aug. 11, 2008, now abandoned.

(60) Provisional application No. 61/166,321, filed on Apr. 3, 2009, provisional application No. 61/245,120, filed on Sep. 23, 2009.

(51) Int. Cl.
  *C12M 1/00*    (2006.01)

(52) U.S. Cl.
  USPC ..................... 435/292.1; 366/342

(58) Field of Classification Search
  CPC ...... C12M 21/02; C12M 31/10; C12M 41/18; C12M 41/24
  USPC ..................... 435/292.1; 366/342
  See application file for complete search history.

(56) References Cited

U.S. PATENT DOCUMENTS

| | | | |
|---|---|---|---|
| 3,439,449 A | 4/1969 | Huff | |
| 5,104,803 A | 4/1992 | Delente | |
| 5,162,051 A | 11/1992 | Hoeksema | |
| 6,279,611 B2 | 8/2001 | Uematsu et al. | |
| 6,370,815 B1 | 4/2002 | Skill | |
| 6,391,238 B1 | 5/2002 | Sato | |
| 6,524,486 B2 | 2/2003 | Borodyanski | |
| 6,579,714 B1 | 6/2003 | Hirabayashi | |
| 6,602,703 B2 * | 8/2003 | Dutil | 435/292.1 |
| 7,331,178 B2 | 2/2008 | Goldman | |
| 2002/0034817 A1 | 3/2002 | Henry | |

(Continued)

FOREIGN PATENT DOCUMENTS

| KR | 20000046481 A | 7/2000 |
|---|---|---|
| KR | 20030018197 A | 3/2003 |
| WO | WO-2005/102031 | 11/2005 |
| WO | WO-2007/025145 | 3/2007 |

(Continued)

OTHER PUBLICATIONS

Huang, Yao-ming, "*Photobioreactor Cultivation of the Cell and Tisse Cultures Derived from Marine Red Macroalga Agardhiella subulata*", A Dissertation submitted to Oregon State University, Mar. 21, 2001, 170 Pages.

(Continued)

*Primary Examiner* — Yogendra Gupta
*Assistant Examiner* — Alison Hindenlang
(74) *Attorney, Agent, or Firm* — Miller, Matthias & Hull LLP

(57) ABSTRACT

A reactor is used to grow a process material, such as algae. The reactor may include fluid-cooled light sources and a movable sparger assembly to increase the effective production volume of the reactor.

15 Claims, 10 Drawing Sheets

(56) References Cited

U.S. PATENT DOCUMENTS

| | | |
|---|---|---|
| 2007/0048848 A1 | 3/2007 | Sears |
| 2007/0048859 A1 | 3/2007 | Sears |
| 2007/0264708 A1 | 11/2007 | Bayless |
| 2007/0289206 A1 | 12/2007 | Kertz |
| 2008/0040970 A1 | 2/2008 | Davanzo |
| 2008/0160593 A1 | 7/2008 | Oyler |
| 2009/0029445 A1 | 1/2009 | Eckelberry et al. |
| 2009/0047722 A1 | 2/2009 | Wilkerson et al. |
| 2009/0291485 A1 | 11/2009 | Shigematsu et al. |

FOREIGN PATENT DOCUMENTS

| | | |
|---|---|---|
| WO | WO-2007/070452 | 6/2007 |
| WO | WO-2009/017677 A2 | 2/2009 |
| WO | WO-2009/142765 A2 | 11/2009 |

OTHER PUBLICATIONS

Hu, Weiwei, "*Characterization of Hydrodynamic Forces and Interfacial Phenomena in Cell Culture Processes*", Dissertation presented to The Ohio State University, 2007, 177 Pages.

\* cited by examiner

REACTOR SYSTEM AND METHOD FOR PROCESSING A PROCESS FLUID

CROSS-REFERENCE TO RELATED APPLICATIONS

This application is a continuation in part of U.S. patent application Ser. No. 12/189,468, filed Aug. 11, 2008. This application also claims the benefit of U.S. Provisional Application Ser. No. 61/166,321, filed Apr. 3, 2009, and U.S. Provisional Application Ser. No. 61/245,120, filed Sep. 23, 2009.

FIELD OF THE DISCLOSURE

This disclosure generally relates to a reactor system and method for processing a process fluid, such as a process fluid having photosynthetic microorganisms. Certain embodiments also relate to a system for producing useful products, such as biofuels and proteins, from the process fluid.

BACKGROUND OF THE DISCLOSURE

Reactor systems are generally known for cultivating and harvesting materials from a process fluid. Some examples of such materials include biomass such as mammalian, animal, plant, and insect cells, as well as various species of bacteria, algae, plankton, and protozoa. These methods and technologies may include open-air systems and closed systems. Algal biomasses, for example, are often cultured in open-air systems (e.g. ponds, lakes, raceway ponds, and the like) that are subject to contamination. These open-air systems are further limited by an inability to substantially control the various process parameters (e.g., temperature, incident light intensity, flow, pressure, nutrients, and the like) involved in cultivating algae.

Alternatively, algae or other material may be cultivated in closed reactor systems, sometimes alternatively referred to as bioreactors. Closed systems allow for better control of the process parameters but are typically more costly to set up and operate. In addition, conventional closed systems are limited in their ability to provide sufficient light to sustain dense populations of photosynthetic organisms cultivated within.

Biomasses have many beneficial and commercial uses including, for example, as pollution control agents, fertilizers, food supplements, cosmetic additives, pigment additives, and energy sources just to name a few. For example, algal biomasses are used in wastewater treatment facilities to capture fertilizers. Algal biomasses are also used to make biofuels.

Bioreactors used for growing photosynthetic organisms typically employ a constant intensity light source. A key factor for cultivating biomasses such as algae in bioreactors is provided in controlling the light necessary for the photosynthetic process. If the light intensity is too high or the exposure time to long, growth of the algae is inhibited. Moreover, as the density of the algae cells in the bioreactors increases, algae cells closer to the light source limit the ability of those algae cells that are further away from absorbing light. This factor has limited the size of conventional, closed bioreactors.

Commercial acceptance of bioreactors is dependent on a variety of factors such as cost to manufacture, cost to operate, reliability, durability, and scalability. Commercial acceptance of bioreactors is also dependent on their ability to increase biomass production, while decreasing biomass production costs. Accordingly, it may be desirable to provide a bioreactor capable of operating at a commercial scale.

SUMMARY OF THE DISCLOSURE

According to certain embodiments, a reactor system for processing a process fluid and adapted for use with a cooling fluid source and a cooling fluid return may include a tank defining an interior space and adapted to receive the process fluid, and a light assembly disposed in the tank interior space and adapted to be submerged in the process fluid. The light assembly may include an outer wall at least partially formed of a translucent material, the outer wall including an open proximal end and a closed distal end, a support disposed inside the outer wall, the support including an outer surface spaced from the outer wall to define an outer chamber and an inner surface defining a fluid tight inner chamber, the inner chamber being configured to define a fluid path having an upstream portion fluidly communicating with the cooling fluid source and a downstream portion fluidly communicating with the cooling fluid return, and a light source coupled to the support outer surface.

Accordingly to additional embodiments, a reactor system for processing a process fluid may include a tank defining an interior space and adapted to receive the process fluid, and a light assembly disposed in the tank interior space and adapted to be submerged in the process fluid. The light assembly may include an outer wall at least partially formed of a translucent material, the outer wall including an open proximal end and a closed distal end, a support disposed inside the outer wall, the support having a proximal end sealingly coupled to the outer wall proximal end and an outer surface spaced from the outer wall to define a light chamber, and a light source coupled to the support outer wall and disposed in the light chamber.

According to still further embodiments, a reactor may include a tank having an inner surface defining an interior space, a light source disposed in the tank interior space and having an exterior surface for emitting light, and a sparger disposed within the tank interior space. The sparger may include a sparger chamber having an inlet fluidly communicating with the source of process gas, an outer periphery sized to move axially within the tank inner surface, a light source aperture extending through the sparger and sized to receive the light source, and a light source nozzle configured to direct a jet of process gas toward the light source exterior surface. A drive may be coupled to the sparger and configured to move the sparger axially within the tank interior chamber.

BRIEF DESCRIPTION OF THE DRAWINGS

For a more complete understanding of the disclosed methods and apparatus, reference should be made to the embodiments illustrated in greater detail on the accompanying drawings, wherein.

It should be understood that the drawings are not necessarily to scale and the disclosed embodiments are sometimes illustrated diagrammatically in partial views. In certain instances, details which are not necessary for an understanding of the disclosed methods and apparatus, or which render other details difficult to perceive, may have been omitted. It should be understood, of course, that this disclosure is not limited to the particular embodiments illustrated herein.

DETAILED DESCRIPTION OF THE DISCLOSURE

Reactor systems and methods are disclosed herein that provide improved light distribution within a reactor tank. In certain embodiments, a light assembly is provided in which a light source is coupled to a support that is disposed within a sealed outer wall. At least a portion of the outer wall is translucent to permit light to project into the tank. The sealed outer wall permits multiple light assemblies to be disposed in the tank when it is filled with a process fluid. In other embodiments, the light assembly further includes a cooling sub-assembly to minimize creation of hot spots within the tank. The cooling sub-assembly may include an inner chamber of the support on which the light source is disposed, wherein the inner chamber defines a cooling fluid flow path. The inner chamber may be fluidly coupled to a cooling fluid source and a cooling fluid return to create a cooling fluid flow through the inner chamber, thereby reducing the amount of heat radiated by the light source. Still further, a sparger may be provided that injects a process gas, such as carbon dioxide, into the reactor tank while simultaneously cleaning the light assembly and/or tank surfaces, thereby to increase the effective volume within the tank that receives light. The sparger may include nozzles directed toward the light assemblies and the tank interior surface, wherein process gas is propelled through the nozzles in the form of pressurized jets that removed debris from the surfaces. While the embodiments disclosed herein are discussed in the context of producing algae, it will be appreciated that the claimed subject matter may be used in other processes, such as growing aerobic and anaerobic yeasts, bacteria, cyano-bacteria, green algae, red algae, brown algae, and purple algae, as well as introducing enzymes to digest synthetic materials, volatile carbon compounds, and biomass.

Figure 1:
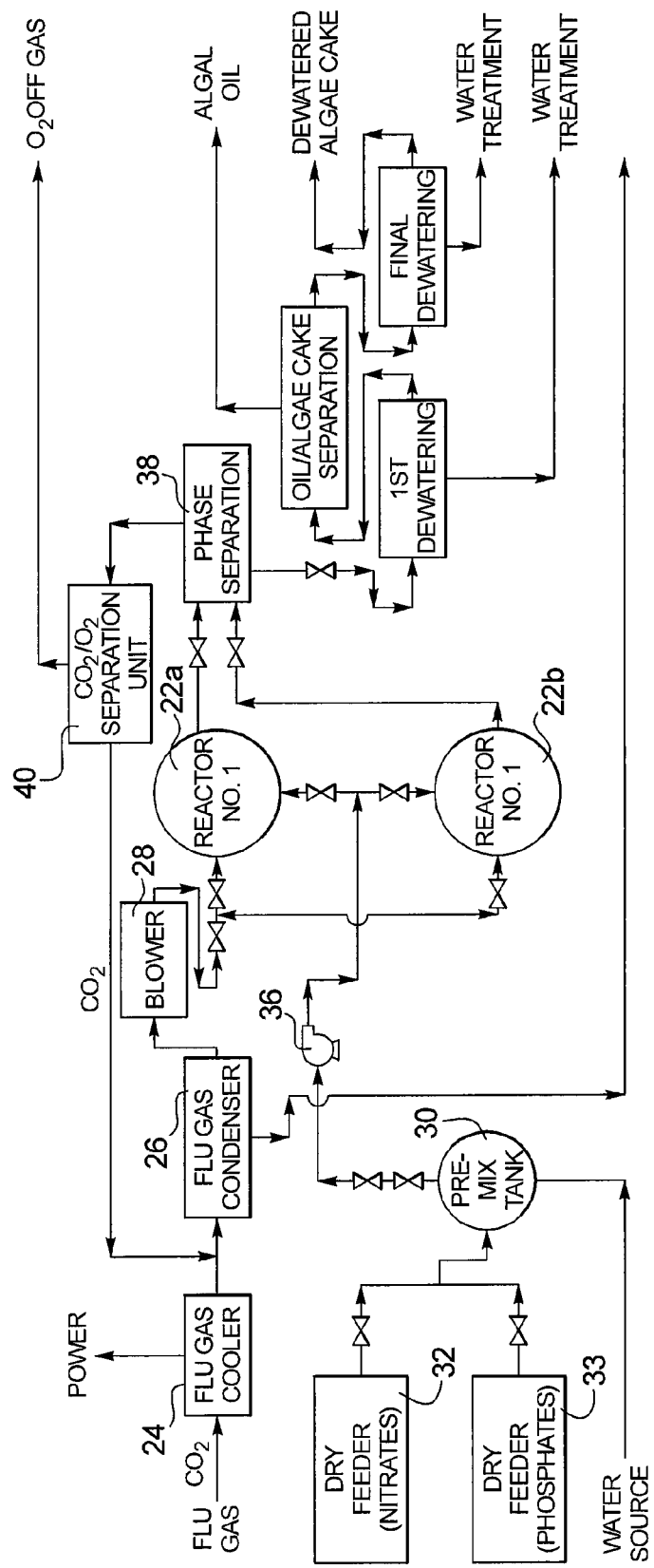
FIG. 1 is a schematic diagram of a material processing system using a pair of reactors.

A system 20 for processing waste streams into usable materials is schematically illustrated in FIG. 1. The system 20 includes a pair of reactors 22a, 22b, each of which may be configured according to one of the embodiments disclosed herein. While two reactors 22a, 22b are shown in FIG. 1, it will be appreciated that a single reactor or more than two reactors may be provided in the system 20. The reactors 22a, 22b may receive waste from various sources, such as gas from a flue gas cooler 24, which may originate from a power generator, such as an organic rankine unit, or other equipment. The gas may be processed prior to discharge into the reactors, such as by condensing water at a condenser 26 and passing through a blower 28. Additionally, nutrients may be provided to the reactors 22a, 22b from a pre-mix tank 30. The pre-mix tank 30 may be coupled to one or more feeders, such as a nitrate dry feeder 32 and a phosphate dry feeder 33. These materials may be mixed in the tank 30 and insoluble organics may be removed. The remaining nutrient-rich material may be fed to the reactors 22a, 22b by a pump 36.

Algae may be discharged from the reactors 22a, 22b to a phase separation tank 38 which separates gases from the solids and liquids. The gases may be fed through a Praxair unit 40 to separate the gases into constituents, such as oxygen and carbon dioxide. The oxygen may be collected for sale or use in other processes and the carbon dioxide may be reused in the system 20. Solids and liquids from the phase separation tank 38 may be discharged to a solids/liquids processor. The solids/liquids processor may include a first dewatering system 40, an oil/algae cake separator 42, and a final dewatering system 44. Liquid from the first dewatering system 40 and the final dewatering system 44 may be collected for treatment. Algal oil may be collected from the oil/cake separator 42, and dewatered algae cake may be obtained from the final dewatering system 44.

Figure 2:
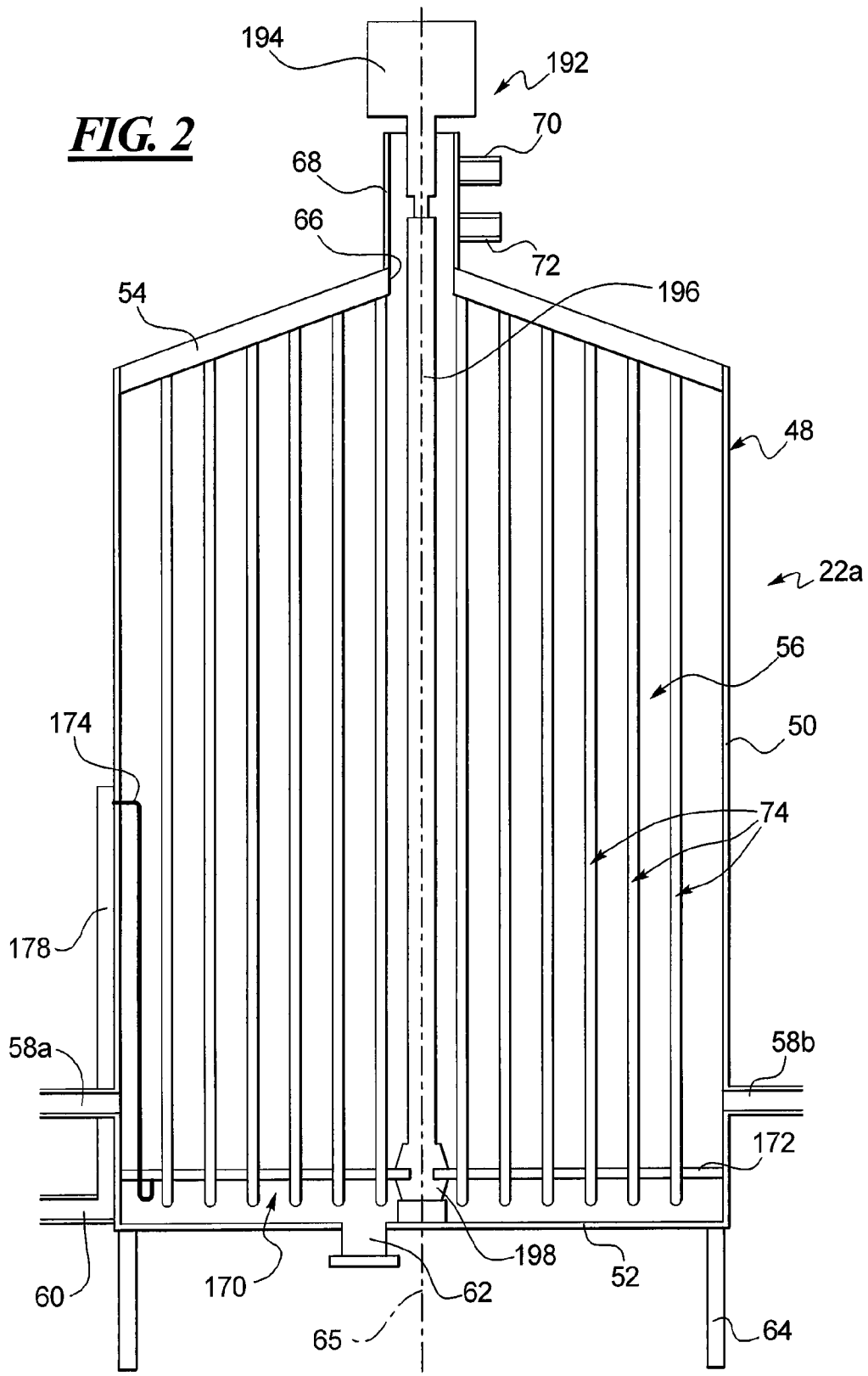
FIG. 2 is a schematic, side elevation view in cross-section of a first embodiment of a reactor used in the system of FIG. 1.
Figure 3:
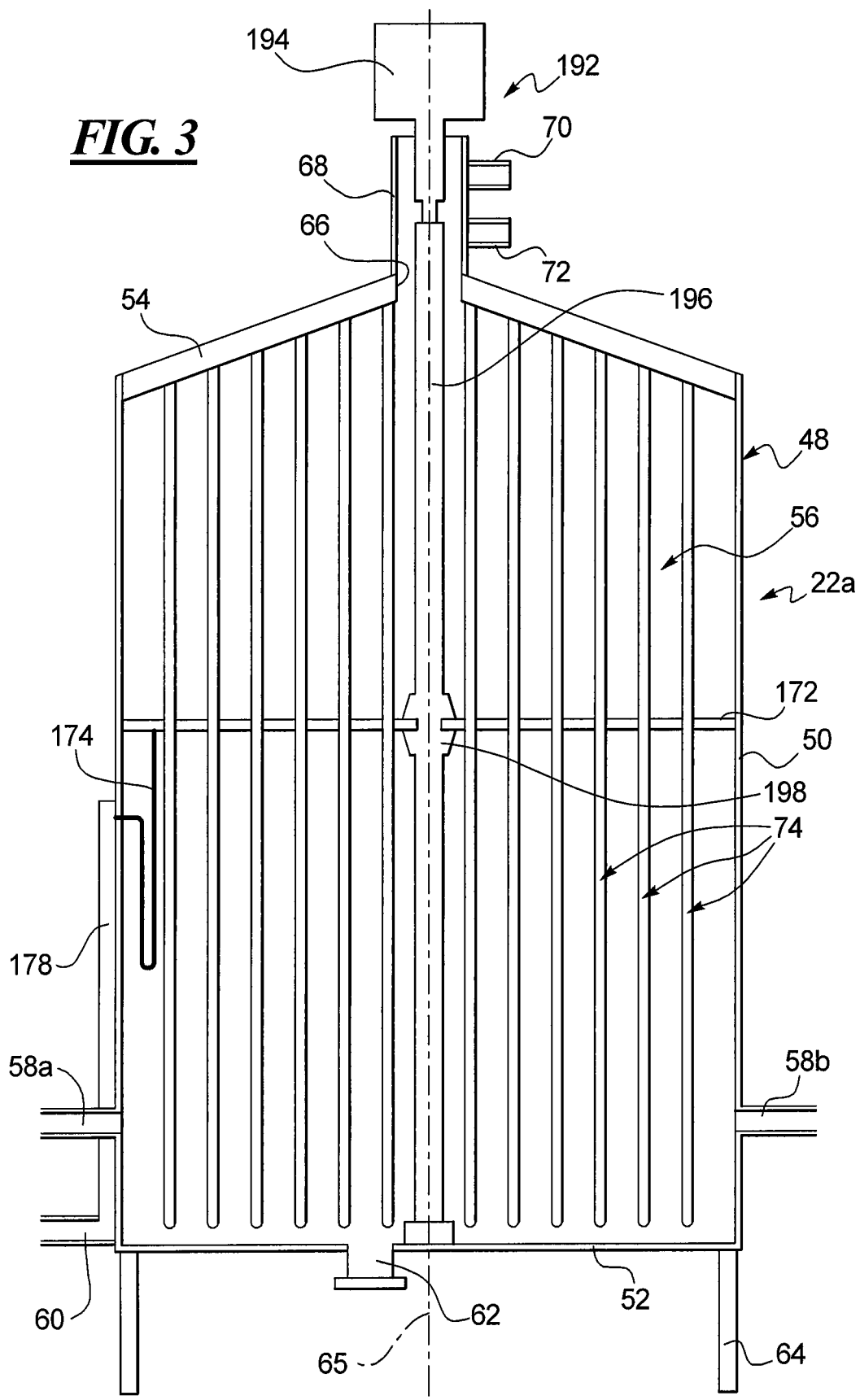
FIG. 3 is a schematic, side elevation view in cross-section of the reactor of FIG. 2 showing a sparger in an elevated position.

An exemplary embodiment of one of the reactors 22a is illustrated in FIGS. 2 and 3. The reactor 22a includes a tank 48 having a side wall 50, bottom wall 52, and top wall 54 defining an interior space 56. The tank 48 may be advantageously constructed to handle an elevated pressure. In some applications, an elevated pressure may assist with the process, such as by increasing assimilation of carbon dioxide by algae to accelerate algae growth. For example, the tank 48 may be pressurized to approximately 35-50 psi; however any pressure that advantageously assists with the process may be used.

The side wall 50 may include water/nutrient inlets 58a, 58b and a process gas inlet 60, each of which fluidly communicates with the tank interior space 56. Multiple water/nutrient inlets 58a, 58b may be provided as shown to promote uniform distribution throughout the tank interior space 56 and to assist with creating a desired fluid flow pattern. The bottom wall 52 may include a drain 62 and a support 64 may extend downwardly from the bottom wall 52 to support the reactor in a vertically upright position (i.e., a longitudinal axis 65 of the reactor is substantially vertical). The top wall 54 may have a conical shape with a central aperture 66 disposed at its apex. The central aperture 66 may communicate between the tank interior space 56 and a central pipe 68. The conical shape of the top wall 54 promotes flow of gas bubbles through the central aperture 66 to the central pipe 68. A gas outlet 70 and an algae outlet 72 fluidly communicate with the central pipe 68.

A plurality of light assemblies 74 is disposed within the tank interior space 56 to promote algae growth. In the illustrated embodiment, the light assemblies 74 are provided as elongate, vertically oriented light tubes 76 spaced throughout the tank interior space 56 (FIGS. 2 and 3). The light tubes 76 may be suspended from the top wall 54 as shown or may be supported in any other suitable fashion. The number and spacing of the light tubes 76 may be selected to maximize an effective tank volume that receives an effective amount of light to promote the desired reaction in the process fluid, such as photosynthesis.

Figure 4:
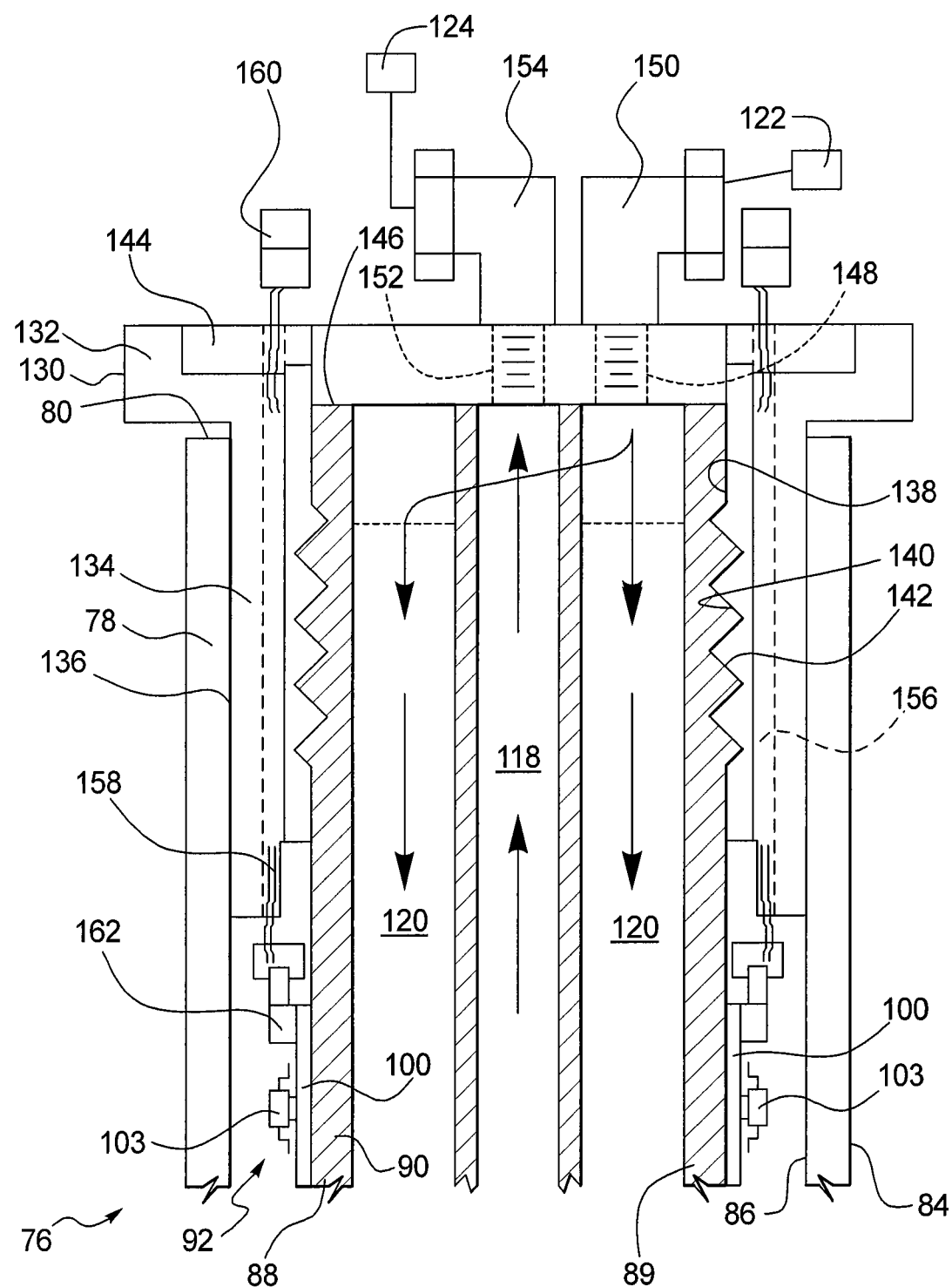
FIG. 4 is an enlarged side elevation view, in cross-section, of a proximal end of a light tube used in the reactor of FIG. 2.
Figure 5:
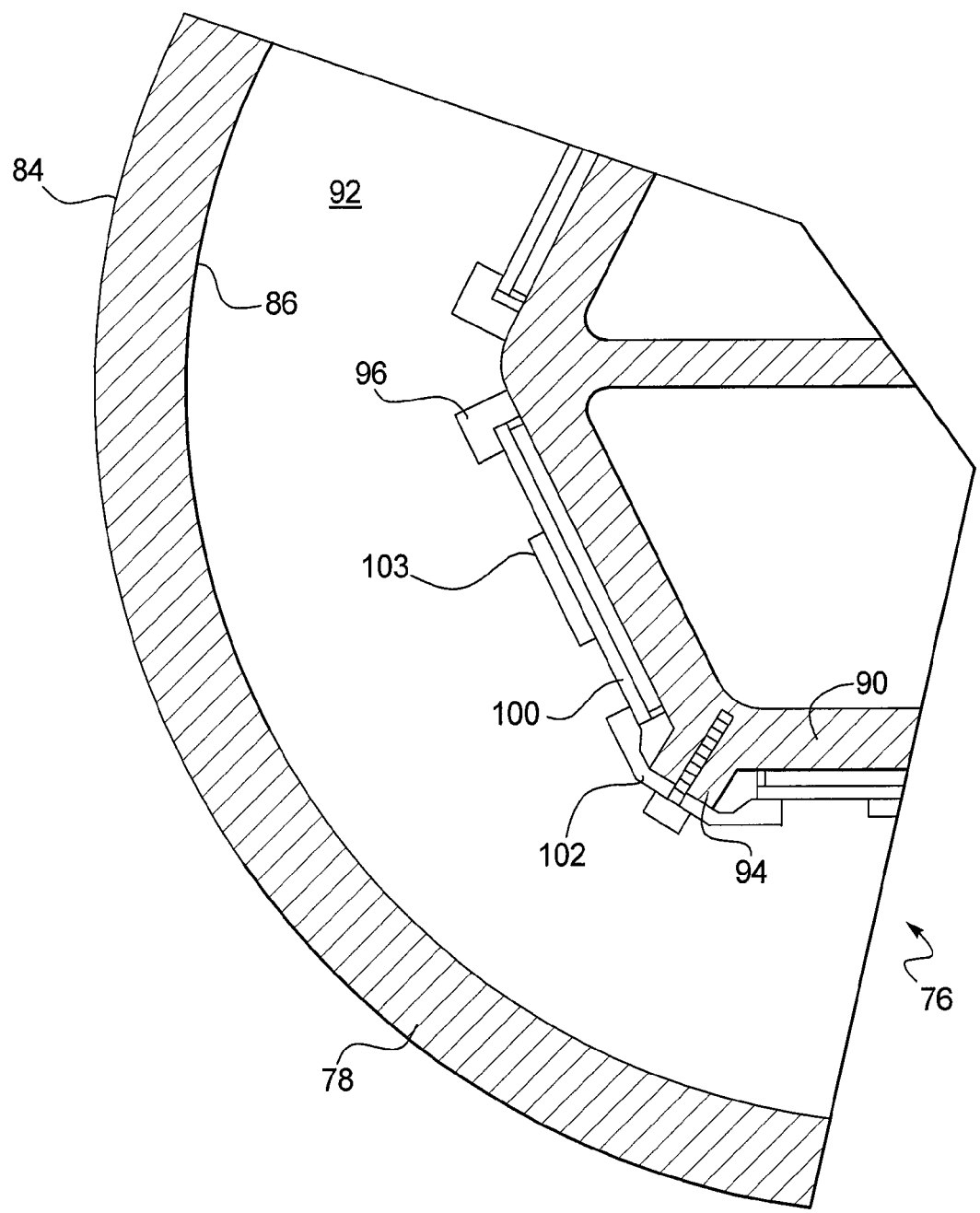
FIG. 5 is an enlarged top view, in cross-section, of a portion of the light tube shown in FIG. 4.
Figure 10:
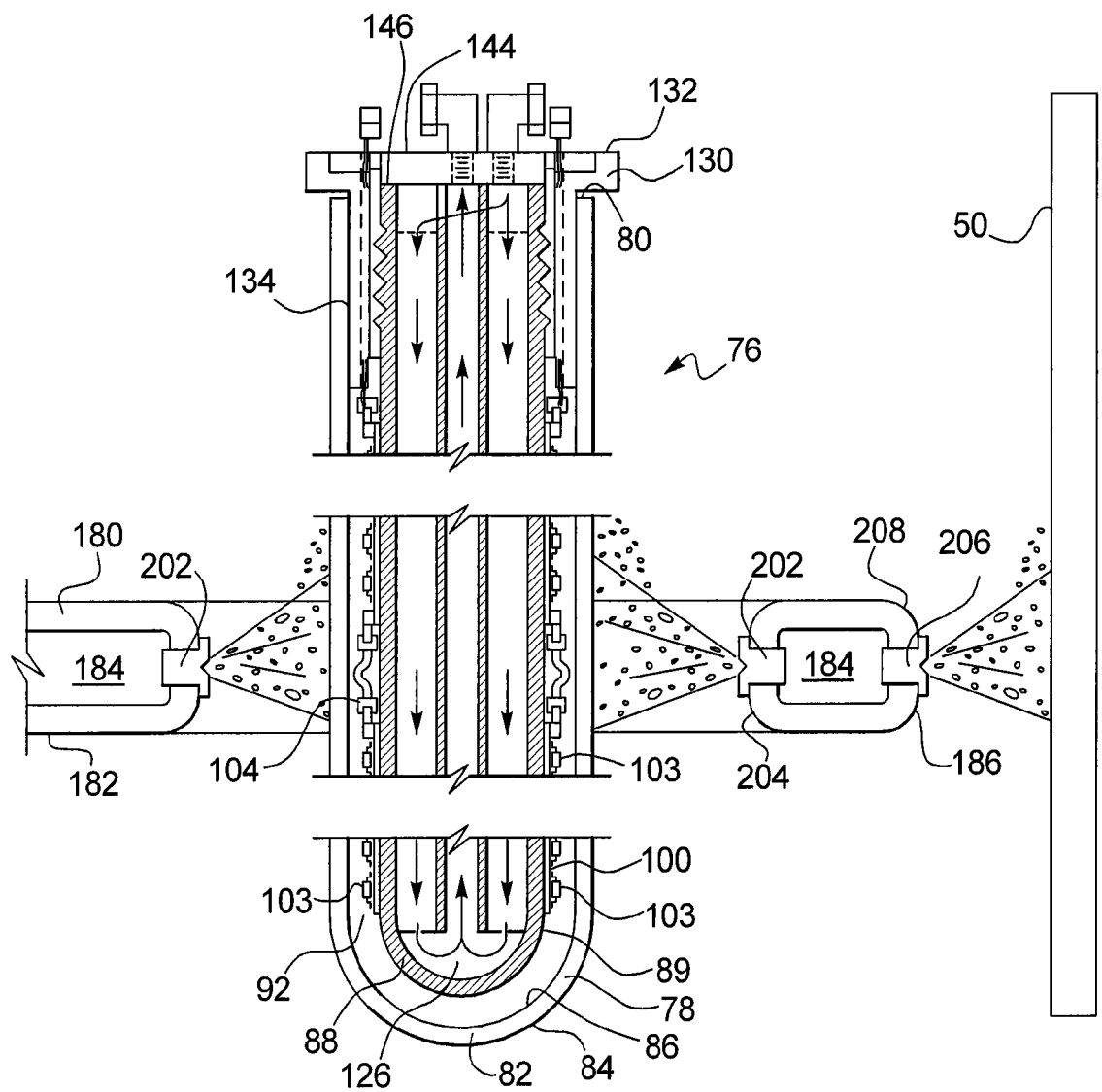
FIG. 10 is an enlarged side elevation view, in cross-section, of the reactor of FIG. 2 showing a portion of the sparger wand of FIG. 8 and the light tube of FIG. 4.

The light tubes 76 may be constructed in a variety of manners. As shown in FIGS. 4, 5, and 10, for example, the light tube 76 includes a generally cylindrical outer wall 78 formed of a translucent, durable material, such as clear PVC. As used herein, a "translucent material" includes any material that permits a sufficient amount of light to pass through the material, and therefore includes translucent, transparent, and other materials. The outer wall 78 has an open proximal end 80 and a closed distal end 82. The outer wall 78 may be cylindrical as shown in FIGS. 4, 5, and 10, or may be hexagonal, triangular, or other shapes. The outer wall 78 defines an exterior surface 84 and an interior surface 86.

Figure 6:
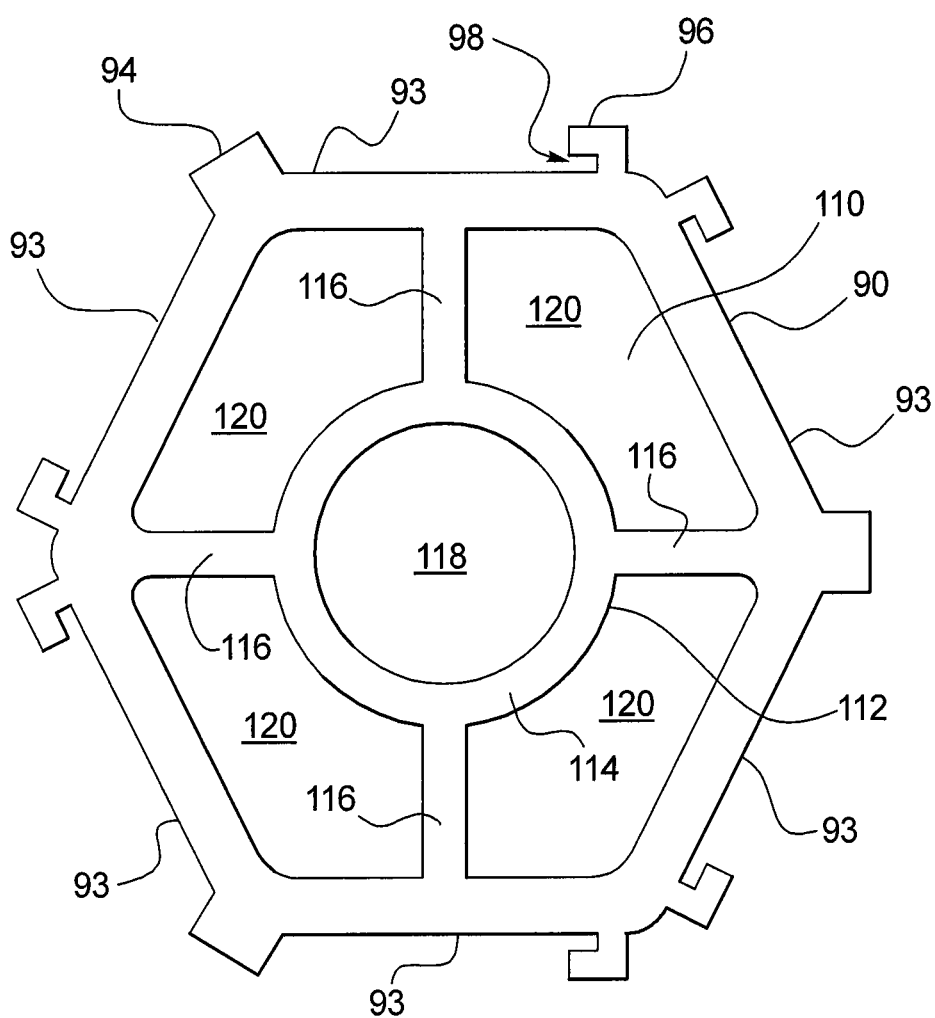
FIG. 6 is an enlarged top view, in cross-section, of a support used in the light tube of FIG. 4.

A support 88 is disposed inside the outer wall 78 and includes an outer surface 89 that is spaced from the outer wall interior surface 86 to define an outer chamber 92. As best shown in FIGS. 5 and 6, the support 88 includes a support wall 90 having a plurality of flat faces 93. The illustrated support wall 90 is hexagonal, however it may be formed in other shapes, including shapes without flat faces 93 such as a cylinder. Support projections 94 and brackets 96 may project outwardly from the support wall 90 to define slots 98.

A circuit board 100 may be inserted into each slot 98 with one end held by the bracket 96 and the other end held by a retainer 102 be coupled to the support projection 94. The circuit board 100 may carry a light source, such as one or more light emitting diodes (LEDs) 103. The LEDs 103 may be spaced as needed to create the desired amount of light inside the tank interior space 56. In some embodiments, for example, the LEDs 103 are spaced approximately 0.5" apart. Multiple circuit boards 100 may be attached along each face 93 of the support and connected by jumper cables 104, as shown in FIG. 10.

The light source may advantageously produce light in selected wavelengths. For example, it has been found that light in the blue and red spectrum are particularly beneficial to algae growth. It is believed that this is so because photosynthesis relies on the penetration of photons into the algae that are absorbed as an energy input to Chlorophyll A and Chlorophyll B, which are the primary chemicals responsible for the photosynthetic production of energy in the form of glucose. Glucose allows the algae cell to function, grow, and divide. The Red spectrum relates primarily to growth of the cell and the blue spectrum relates to division of the cell that causes the exponential multiplication of cells for total mass growth. The light may be directly provided in the desired color spectrum, or a filter may be used so that only the desired light spectrum is delivered to the algae.

A cooling sub-assembly may be provided to reduce the amount of heat emanating from the light assembly 74. In an embodiment illustrated in FIG. 6, the support wall 90 may further define an inner chamber 110 defining a cooling fluid flow path. An internal baffle 112 extends through the inner chamber 110 and includes an inner tube 114 and four webs 116 extending between the inner tube 114 and the support wall 90. The inner tube 114 defines an inner conduit 118, while the webs 116 define outer conduits 120 extending between the inner tube 114 and the support wall 90 and surrounding the inner conduit 118. As best shown in FIG. 4, the outer conduits 120 form an upstream portion of the flow path that fluidly communicates with a cooling fluid source 122, while the inner conduit 118 forms a downstream portion of the flow path that fluidly communicates with a cooling fluid return 124. The outer conduits 120 may fluidly communicate with the inner conduit 118 at a distal end 126 of the support 88, as best shown in FIG. 10. A cooling fluid, such as water, may flow along the cooling fluid flow path to absorb heat generated by the LEDs 103, thereby to reduce the amount of heat added to the tank interior space 56 by the light assemblies 74. Additionally, the support 88 may be formed of a material having a high heat transfer coefficient, such as aluminum, to facilitate heat absorption by the cooling fluid.

Figure 7:
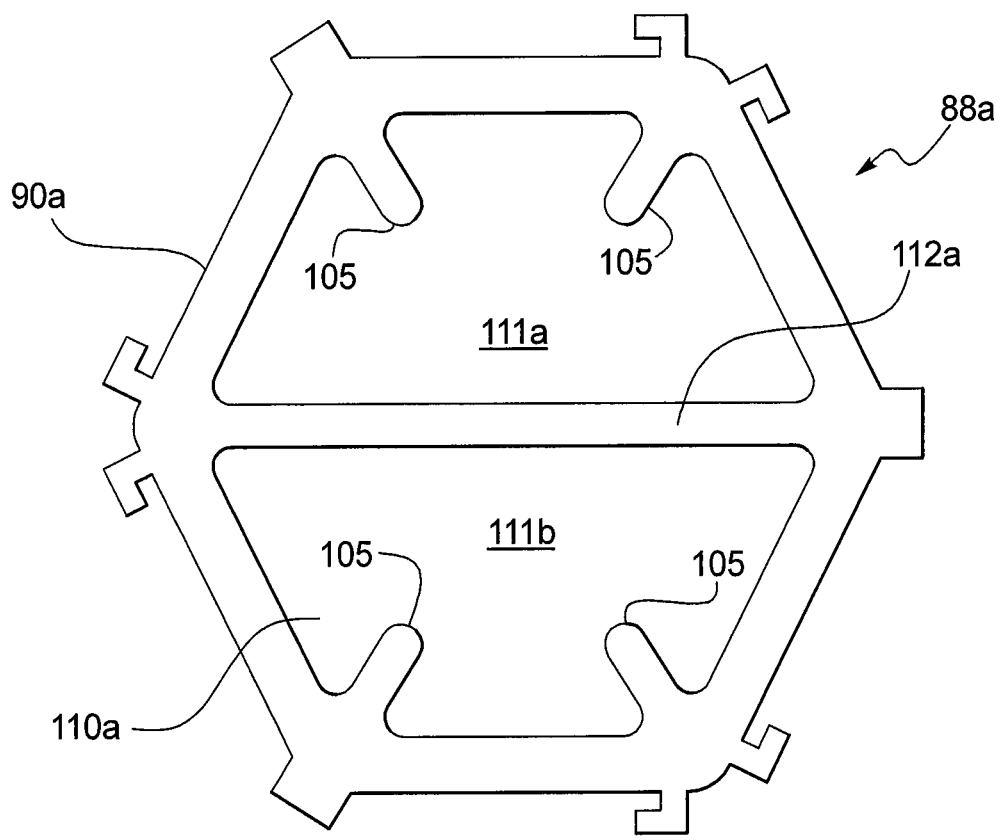
FIG. 7 is an enlarged top view, in cross-section, of an alternative support usable in the light tube of FIG. 4.

An alternative support 88a is illustrated in FIG. 7 having a modified internal baffle 112a. A support wall 90a of the support 88a defines an inner chamber 110a which forms a cooling fluid flow path. The internal baffle 112a divides the inner chamber 110a into two chamber portions 111a, 111b. Chamber portion 111a may form an upstream portion of the fluid flow path that fluidly communicates with the cooling fluid source 122, while chamber portion 111b may form a downstream portion of the flow path that fluidly communicates with the cooling fluid return 124. The support 88a further includes heat sink projections 105 extending into the inner chamber 110a to further promote heat transfer to the cooling fluid.

Each light tube 76 may further include a wall flange 130 to seal between the outer wall 78 and the support 88. As best shown in FIG. 4, the wall flange 130 includes a flange head 132 and a collar 134. The collar 134 has an outer surface 136 sized to closely fit the outer wall interior surface 86 to facilitate a fluid-tight seal therebetween. An inner surface 138 of the wall flange 130 is formed with internal threads 140 configured to engage external threads 142 formed in the support outer surface 89, thereby to facilitate a fluid-tight seal therebetween. Accordingly, the outer chamber 92 formed between the support outer surface 89 and the outer wall interior surface 86 is sealed from the environment exterior to the outer wall 78, thereby permitting use the light tube 76 to be submerged in the process fluid inside the tank 48.

Each light tube 76 may further include a support flange 144 coupled to a proximal end 146 of the support 88. The support flange 144 may further be coupled to the wall flange 130 to further seal the outer chamber 92. In the embodiments illustrated in FIGS. 4 and 10, the support flange 144 includes an inlet port 148 with an inlet fitting 150 and an outlet port 152 with an outlet fitting 154 to facilitate connection to the cooling fluid source 122 and cooling fluid return 124, respectively.

A wire channel 156 may be formed through the support flange 144 and/or wall flange 130 to permit connection of the circuit board 100 to an electrical source. As best shown in FIG. 4, a lead wire 158 extends through the wire channel 156 and has a first and connected to an electrical connector 160 and a second end connected to a board connector 162.

Returning to FIGS. 2 and 3, a sparger sub-system 170 is provided for injecting a process gas, such as carbon dioxide, into the tank interior space 56. The sparger sub-system 170 includes a sparger wand 172 and flexible conduit 174. A fixed conduit 178 may extend at least partially up the tank side wall 50 to connect the flexible conduit 174 to the process gas inlet 60. The flexible conduit 174, in turn, fluidly communicates with the sparger wand 172. As described in greater detail below, the sparger wand 172 may include apertures or nozzles for discharging additional process gas into the tank 48. The sparger wand 172 may further be movable within the tank 48 in an axial direction. FIG. 2 shows the sparger wand 172 in a bottom position while FIG. 3 shows the sparger wand 172 in an intermediate position.

Figure 8:
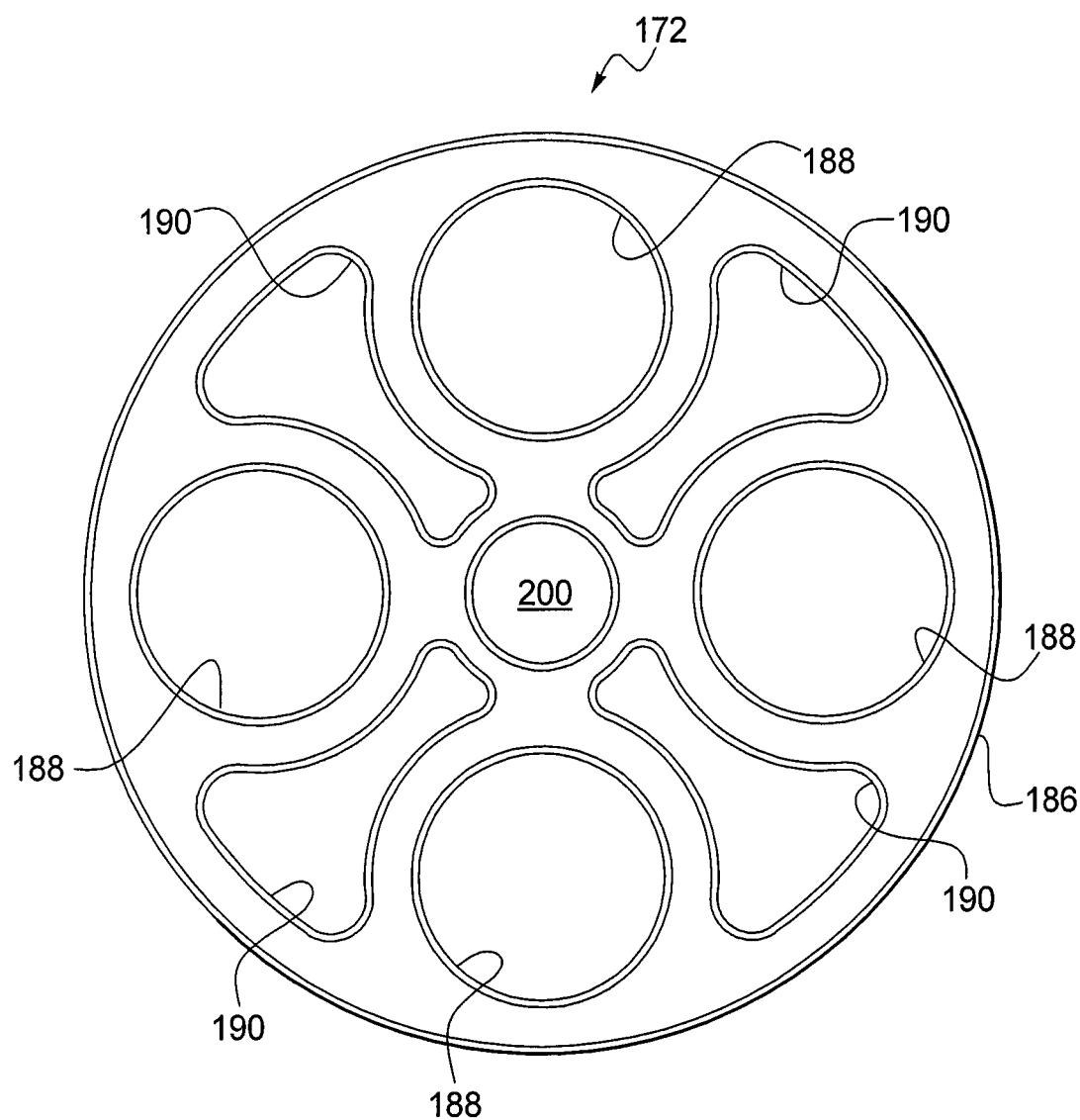
FIG. 8 is a top view of a sparger wand used in the reactor of FIG. 2.
Figure 9:
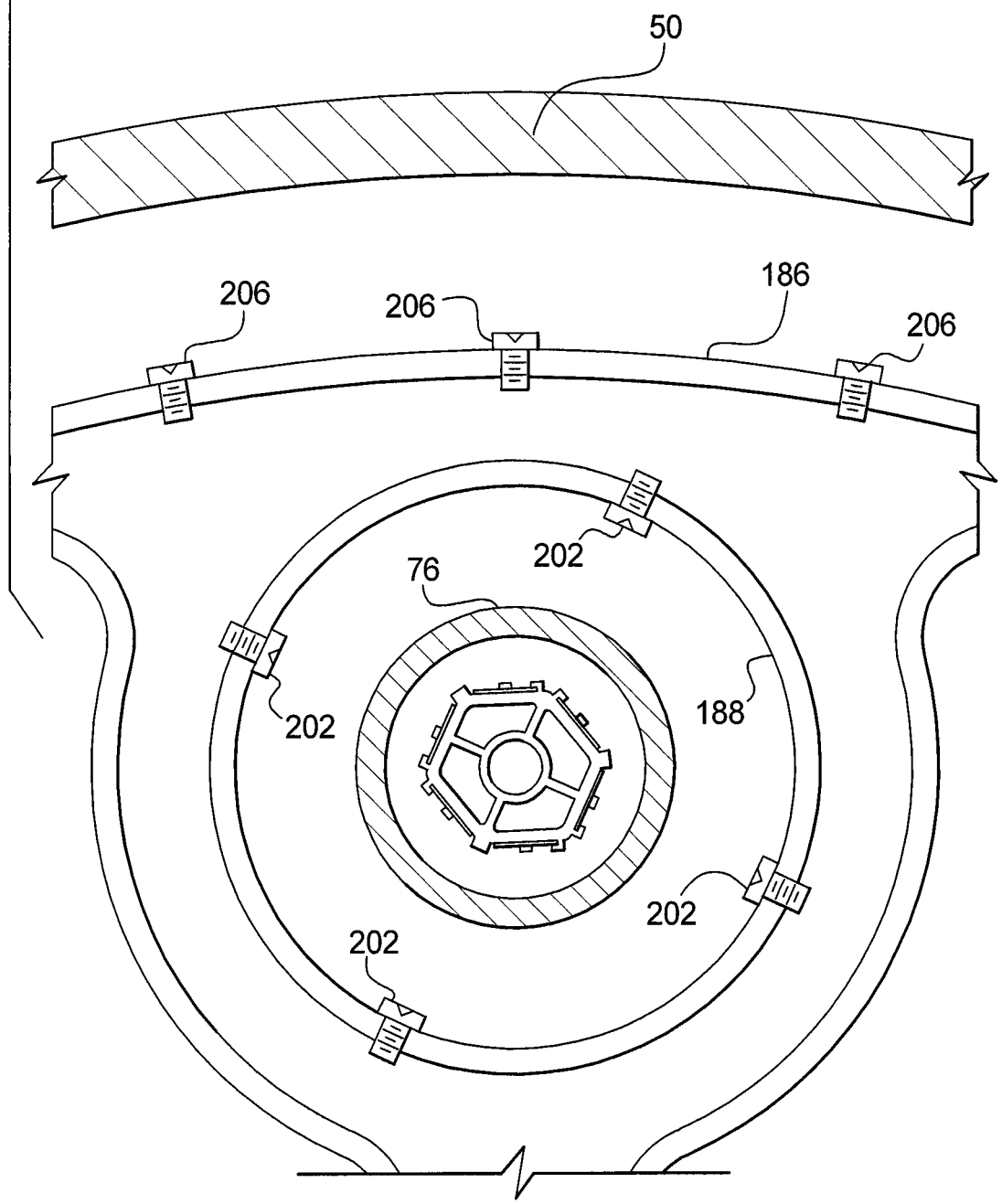
FIG. 9 is an enlarged plan view, in cross-section, of the reactor of FIG. 2 showing a portion of the sparger wand of FIG. 8 and the light tube of FIG. 4.

The sparger wand 172 is illustrated in greater detail in FIGS. 8-10. The sparger wand 172 includes spaced upper and lower walls 180, 182 (FIG. 10) defining a sparger chamber 184 therebetween. The sparger chamber 184 fluidly communicates with the flexible conduit 174. The sparger wand 172 has an outer periphery 186 sized to create a gap between the sparger wand 172 and the tank side wall 50 (FIGS. 8 and 9), thereby to permit axial movement of the sparger wand 172 within the tank 48. The sparger wand 172 may further include light source apertures 188 sized to accommodate the light tubes 76. Additionally, fluid passage apertures 190 may be formed through the sparger wand 172 to reduce the impact of the sparger wand 172 on fluid flow within the tank 48 and to reduce resistance to axial movement of the sparger wand 172 within the tank 48 when it full of process fluid.

A drive 192 is operatively coupled to the sparger wand 172 to move the sparger wand 172 axially within the tank 48. As best shown in FIGS. 2 and 3, the drive 192 includes a motor 194 operatively coupled to a rotatable threaded rod 196. A coupling 198 is operatively connected to the threaded rod 196 and engages the sparger wand 172 adjacent a rod aperture 200 formed in the sparger wand 172. The threaded rod 196 may be rotated in a first direction to raise the coupling 198 and sparger wand 172 connected thereto, and in a second direction to lower the coupling 198 and sparger wand 172.

The sparger wand 172 may further include nozzles configured to produce jets of process gas that clean surfaces within the tank 48. As best shown in FIGS. 9 and 10, the sparger wand 172 may include light source nozzles 202 oriented to direct a jet of process gas toward a selected light tube 76. In the illustrated embodiment, the light source nozzles 202 are coupled to an edge 204 of the light source aperture 188 and directed radially inwardly from the aperture 188 toward the light tube 76. While FIG. 9 illustrates four light source nozzles 202 associated with a single light tube aperture 188, fewer or more nozzles may be provided. The light source nozzles 202 may be configured to generate jets of process gas having sufficient velocity to remove debris from the exterior surface of the light tube 76, thereby to maintain or increase the volume of the tank 48 receiving sufficient light.

The sparger wand 172 may also have tank nozzles 206 configured to direct a jet of process gas toward an inner surface of the tank side wall 50. As shown in FIGS. 9 and 10, the outer periphery 186 may be formed with a radially outwardly facing edge 208. The tank nozzles 206 may be coupled to the periphery edge 208. The tank nozzles 206 may be configured to generate jets of process gas sufficient to remove debris from the inner surface of the tank side wall 50. The light source nozzles 202 and tank nozzles 206 also promote distribution of the process gas throughout the entire volume of the tank and improve mixing within the tank, thereby enhancing and/or accelerating the reactor process.

The conduits for introducing liquid and gas into the tank 48 may be configured to produce a desired fluid flow path within the tank 48. For example, the water/nutrient inlets 58a, 58b may be positioned, sized, oriented, or otherwise configured to produce a desired fluid flow path inside the tank 48. In certain applications, it may be advantageous to configure the inlets/apertures to produce a helical or swirl shaped flow path. In other embodiments, a random flow path may be used. The particular flow path may be suited to the type of product being processed in the tank. Algae applications, for example, may benefit from a fluid flow path that increases the amount of algal cells that pass sufficiently close to the light sources. Such a flow path may have a helical, random, or other shape.

While only certain embodiments have been set forth, alternatives and modifications will be apparent from the above description to those skilled in the art. These and other alternatives are considered equivalents and within the scope of this disclosure and the appended claims.

What is claimed is:

1. A reactor system for processing a process fluid and adapted for use with a cooling fluid source and a cooling fluid return, comprising:
    a tank defining an interior space and adapted to receive the process fluid;
    a light assembly disposed in the tank interior space and adapted to be submerged in the process fluid, the light assembly comprising:
        an outer wall at least partially formed of a translucent material, the outer wall including an open proximal end and a closed distal end;
        a support disposed inside the outer wall, the support including an outer surface spaced from the outer wall to define an outer chamber and an inner surface defining a fluid tight inner chamber, the inner chamber being configured to define a fluid path having an upstream portion fluidly communicating with the cooling fluid source and a downstream portion fluidly communicating with the cooling fluid return; and
        a light source coupled to the support outer surface.

2. The reactor system of claim 1, in which the light source comprises at least one light emitting diode.

3. The reactor system of claim 2, further comprising a circuit board coupled to the support outer surface, in which the at least one light emitting diode is mounted on the circuit board.

4. The reactor system of claim 1, further comprising a wall flange sealingly coupled to the outer wall proximal end and configured to sealingly engage the support, and a support flange sealingly enclosing the support inner chamber and defining a cooling fluid inlet port for fluidly communicating between the fluid path upstream portion and the cooling fluid source and a cooling fluid outlet port for fluidly communicating between the fluid path downstream portion and the cooling fluid return.

5. The reactor system of claim 4, in which a wire channel extends through the wall flange and the support flange, and in which a lead wire extends through the wire channel.

6. The reactor system of claim 1, in which the support includes at least one heat sink projection extending into the inner chamber.

7. The reactor system of claim 1, in which the support includes an internal baffle configured to separate the inner chamber into an upstream chamber and a downstream chamber.

8. The reactor system of claim 1, in which the support includes an internal baffle extending through the inner chamber, the internal baffle defining an inner conduit and at least one outer conduit surrounding the inner conduit.

9. The reactor system of claim 1, in which the cooling fluid comprises water.

10. The reactor system of claim 1, in which the process fluid comprises an algae biomass, and in which the light source is configured to promote algae growth within the algae biomass.

11. A reactor system for processing a process fluid, comprising:
    a tank defining an interior space and adapted to receive the process fluid;
    a light assembly disposed in the tank interior space and adapted to be submerged in the process fluid, the light assembly comprising:
        an outer wall at least partially formed of a translucent material, the outer wall including an open proximal end and a closed distal end;
        a support disposed inside the outer wall, the support having a proximal end sealingly coupled to the outer wall proximal end and an outer surface spaced from the outer wall to define a light chamber; and
        a light source coupled to the support outer wall and disposed in the light chamber.

12. The reactor system of claim 11, in which the light source comprises at least one light emitting diode.

13. The reactor system of claim 12, further comprising a circuit board coupled to the support outer surface, in which the at least one light emitting diode is mounted on the circuit board.

14. The reactor system of claim 11, in which the process fluid comprises an algae biomass, and in which the light source is configured to promote algae growth within the algae biomass.

15. The reactor system of claim 11, in which the reactor system further includes a cooling fluid source and a cooling fluid return, and in which the support further defines a fluid tight inner chamber, the inner chamber being configured to define a fluid path having an upstream portion fluidly communicating with the cooling fluid source and a downstream portion fluidly communicating with the cooling fluid return.

* * * * *